United States Patent [19]
Rossman et al.

[11] Patent Number: 5,549,247
[45] Date of Patent: Aug. 27, 1996

[54] SCENTED LIQUID NEBULIZER

[75] Inventors: Jon R. Rossman, Chelmsford; Bryan Hotaling, Arlington, both of Mass.

[73] Assignee: Leyden House Limited, Leyden, Mass.

[21] Appl. No.: 364,250

[22] Filed: Dec. 27, 1994

[51] Int. Cl.$^6$ .............................. A61L 9/14; B05B 7/24
[52] U.S. Cl. .............................. 239/57; 239/58; 239/34; 239/338
[58] Field of Search ..................... 239/34, 57–59, 239/125, 318, 338

[56] References Cited

U.S. PATENT DOCUMENTS 4,836,452  6/1989  Fox ................................. 239/338
5,248,448  9/1993  Waldron et al. ................. 239/338 X

FOREIGN PATENT DOCUMENTS 1054110  2/1954  France ............................. 239/34
 351240  2/1961  Switzerland ..................... 239/34

*Primary Examiner*—Andres Kashnikow
*Assistant Examiner*—Lesley D. Morris
*Attorney, Agent, or Firm*—William Nitkin

[57] ABSTRACT

An air nebulizer to be attached to a bottle containing scented liquid with a housing structure to receive air under pressure to cause the scented liquid to come out of the bottle under pressure and pass through a mesh in the housing to create a fine mist to be dispersed through an adjustable opening in the housing, the size of which opening controls the amount of such mist dispersed into the ambient atmosphere.

4 Claims, 3 Drawing Sheets

SCENTED LIQUID NEBULIZER

BACKGROUND OF THE INVENTION

1. Field of the Invention

The device of this invention resides in the area of devices which impart a pleasing scent to the surrounding ambient atmosphere and more particularly relates to an electric nebulizing device which imparts an aroma to a room.

2. Description of the Prior Art

It is often desirable to impart a pleasant aroma to a room such as in hospitals, nursing homes, work environments and the like. Pleasing scents can have beneficial effects on individuals which not only make them feel better but also cause them to react positively to their surroundings. Scented aromatic fluids, such as essential oils, can be sprayed in a room from aerosol cans. Containers containing an aromatic chemical with wicks placed into such chemical to promote the aromatic fluid's evaporation can also impart aroma to the surrouding air. Other devices of the prior art have chambers containing the scented material in a gel or solid form which when such device is opened, the ambient atmosphere flows through such chamber and evaporates the scented gel/solid material to disperse the scent throughout the room. Yet still another device provides a heater element which heats aromatic material which can be a liquid, gel or solid but which, when heated, evaporates and provides its aroma to the surrounding ambient atmosphere. Electronic devices for providing various aromas to the atmosphere also exist which devices pump air through or near aromatic liquids to help carry their scent into a room. Also, aromatic scents can be utilized in air conditioning units and humidifiers which scents are added thereto to be carried by the normal air flow of such units into the room or area as desired.

SUMMARY OF THE INVENTION

It is an object of this invention to provide an improved electrical air odorizing device which includes an air pump held within a casing, such pump producing pressurized air and with a portion of the casing formed in a shape to hold upright a bottle having a screw-type top and containing aromatic scented liquid, such scent to be dispersed throughout an area such as a room. A hose member extends from the air pump, out the casing to the device of this invention which has a housing. The housing has a threaded portion at its bottom onto which the top of the bottle containing essential oils or other liquid scent is screwed, which bottle is then held upright within the portion of the air pump casing. The pressurized air is then passed through the hose member into the housing and moves by an upper aperture in a nozzle member within a chamber in the housing to cause a reduction in air pressure above the nozzle member. A tube extends from a bottom aperture in the nozzle member into the scented liquid in the bottle. A low air pressure is created in the chamber immediately above the nozzle member and causes the scented liquid to be pushed upwards from the bottle by the higher normal atmospheric air pressure in the bottle through the tube and nozzle member, through an aperture at the top of the chamber, into the housing to be forced as a fine mist out an adjustably sized opening near the top of the the housing to be dispersed within the room.

It is a further object of this invention both to control the amount of scented air provided to the room and to provide such scented air as a fine mist so that it is more easily and quickly dispersed throughout the room.

It is a still further object of this invention once the device is shut off, to provide a downward drainage of the scented liquid back into the bottle for reuse and to prevent various apertures and surfaces within the device from becoming plugged and caked with dried-up scented material.

In order to accomplish the goals of this invention, the device further includes a mesh member placed within the housing which mesh member causes the scent particles to become more finely dispersed as a fine mist before they leave the housing. The nozzle member is generally centrally disposed along a vertical axis 63 within the chamber which chamber is partially surrounded by a drain aperture located in the bottom portion of the housing so that when the device is turned off, any air-borne scented vapors within the housing coalesces to form droplets within the mesh member which then drain back through the drain aperture into the bottle for later reuse. Further, a movable door is located in the opening at the top of the housing and is manually openable to varying positions which door positioning controls the size of the opening and therefore the amount of scent that is dispersed into the room.

DESCRIPTION OF THE PREFERRED EMBODIMENT(S)

Figure 1:
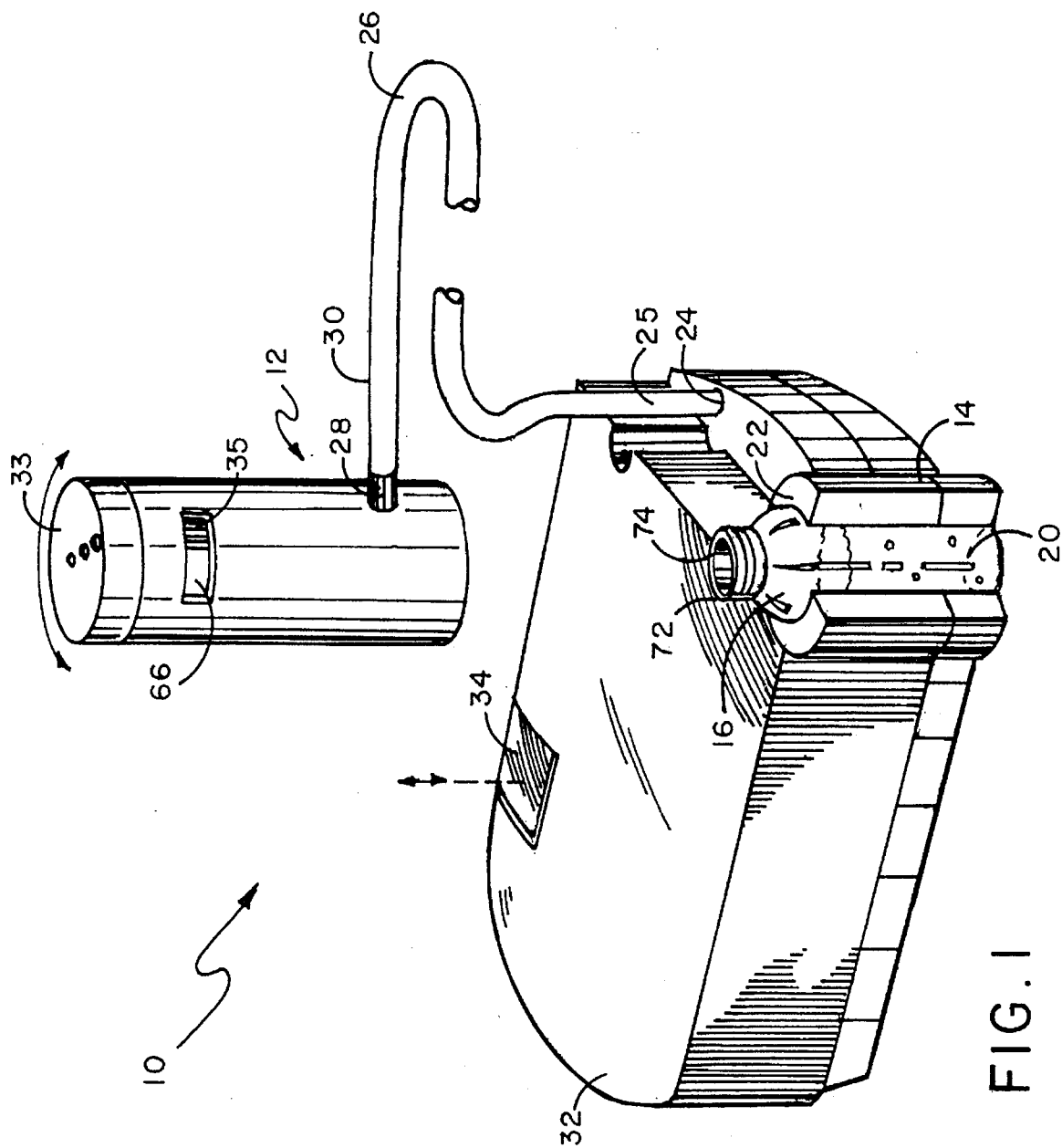
FIG. 1 illustrates a perspective view of the housing of the Scented Liquid Nebulizer of this invention attached to an air hose extending from an air pump within a casing, such housing disposed above a bottle containing scented liquid.

FIG. 1 illustrates a perspective view of the scented liquid nebulizer 10 of this invention, the basic structure of which includes casing 32 in which is disposed an air pump, not seen, and housing 12. The device can be activated by means of on/off switch 34 located on the casing. The device can operate by electricity or equivalent power means. Pressurized air is provided at casing opening 24 and passes through the first end 25 of hose member 26. Holder 14 can be a portion of casing 32 formed in a semi-circle 22 adapted to receive snugly therein bottle 20, holding it upright for use. Hose member 26 extends and is engaged at its second end 30 to inlet 28 of housing 12 which housing can be screwed onto threads 72 of opening 74 at the top of bottle 20 until bottle seat 58 of housing 12, seen in FIG. 2, meets the inside of opening 74 of bottle 20, sealing the housing to the bottle. Bottle 20 can contain essential oils 16, other aromatic scented liquid or equivalent.

Figure 2:
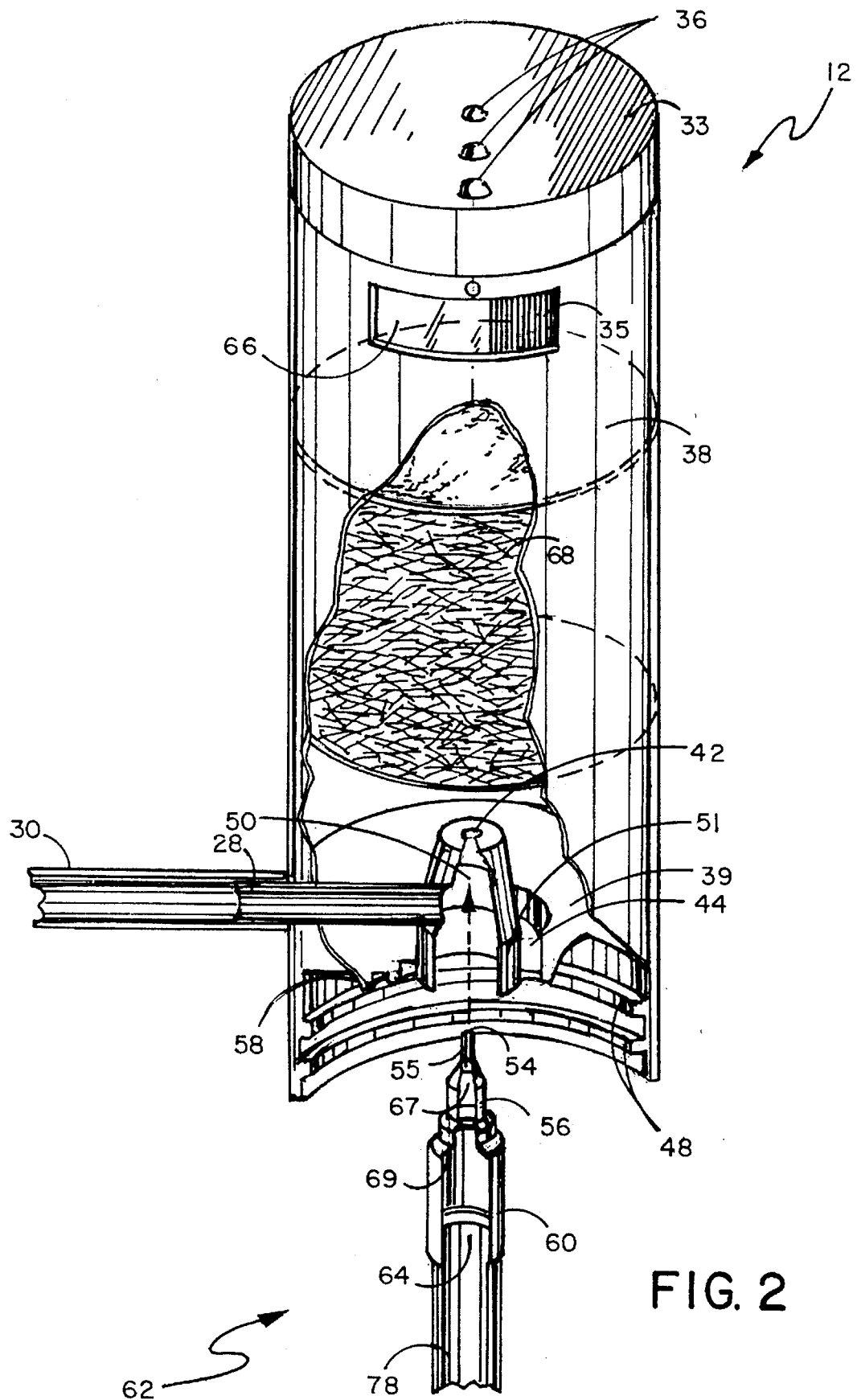
FIG. 2 illustrates a cutaway perspective view of the housing and nozzle member of the device of this invention.
Figure 3:
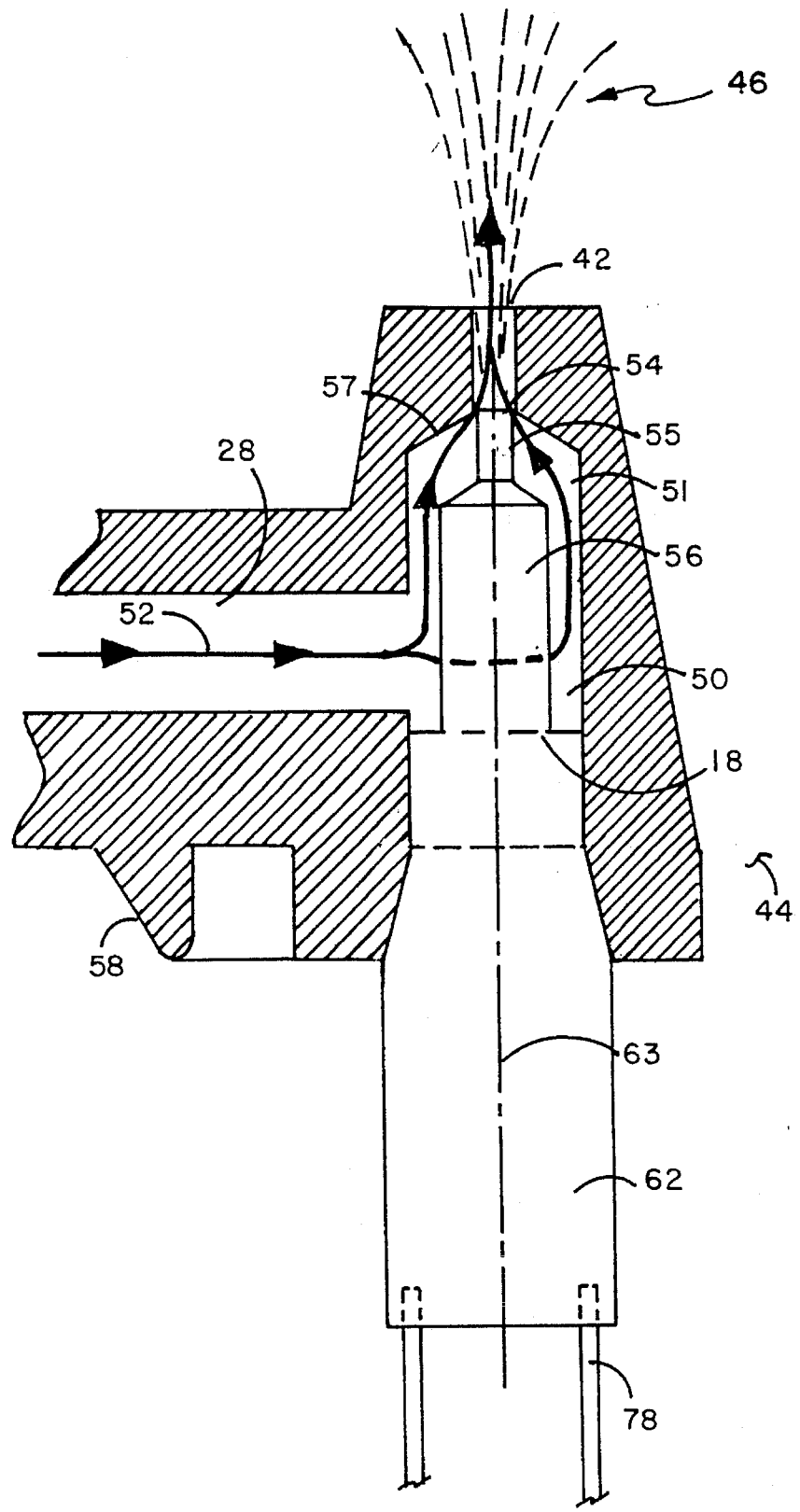
FIG. 3 illustrates a side partial cross-sectional view showing the nozzle member disposed within the chamber.

FIG. 2 illustrates a cutaway perspective view of housing 12 which, in a preferred embodiment, is a cylindrical container having an interior portion anti side wall 38 with inlet 28 onto which the second end 30 of hose member 26 is engaged by slipping it over inlet 28 such that pressurized air is directed into chamber 50. Nozzle member 62 is disposed within chamber 50 of chamber housing 51 above threaded portion 48 at the bottom portion of housing 12, which threaded portion 48 is engageable onto threads 72 of bottle 20 as seen in FIG. 1. Chamber housing 51 has a chamber aperture 42 at its top. Pressurized air passing through inlet 28 is directed into chamber 50, as also seen in FIG. 3, and passes around upper cylindrical portion 56 of nozzle member 62 which is narrower in diameter than the diameter of chamber 50 and passes by nozzle member top opening 54 and out chamber aperture 42. The pressurized air cannot pass down into bottle 20 as chamber 50 is blocked at its bottom by shoulder 18 of nozzle member 62. As seen in FIGS. 2 and 3, a tube 78 extends from the bottom of nozzle member 62 and extends downward, not seen, into scented fluid 16 in bottle 20. Bottle seat 58, seen in FIG. 2, seals against the inside of opening 74 of bottle 20. The pressurized air traveling through chamber 50 and exiting through chamber aperture 42 just above nozzle opening 54 causes a reduction of the air pressure above nozzle member top opening 54 by the venturi effect in chamber 50, causing scented fluid 16 in bottle 20 to be forced up tube 78 by the greater normal atmospheric air pressure in bottle 20 and out nozzle member top opening 54 and through chamber aperture 42 as a pressurized mist into housing 12. The size of nozzle member top opening 54, being smaller than chamber aperture 42, and the closeness of the chamber aperture to the nozzle member top opening 54 aid in creating a venturi effect on the fluid exiting from chamber opening 42 in the form of such pressurized mist 46. The closeness of chamber housing upper walls 57 to nozzle member top opening 54 directs the air flow 52 over nozzle member top opening 54. As seen in FIG. 2, nozzle tip 55 of nozzle member 62 under nozzle member top opening 54 extends downwardly to upper cylindrical portion 56 by first downwardly and outwardly sloping wall 67 which shape helps to promote downward drainage of scented liquid when the device is turned off. Upper cylindrical portion 56 further extends down to lower cylindrical portion 60, forming second outwardly and downwardly inner sloping wall 69 which sloping wall also promotes downward drainage of the scented liquid such that the scented liquid will easily drain out of nozzle member bottom opening 64, down tube 78 and into bottle 20. Nozzle member 62 can be metal, such as brass, while the rest of the structure can be made of plastic or equivalent.

The pressurized mist 46, as illustrated in FIG. 3, carries the scent and passes through fine mesh member 68 disposed within housing 12 which passage further disperses the scented mist to become even further atomized into a fine mist which then passes out housing opening 35 disposed in the top portion of housing 12, seen in FIG. 2. Housing opening 35 can be manually opened or closed by adjustable door 66 which in one embodiment extends downward from rotatable cap 33. As seen in FIG. 2, by rotating cap 33 counterclockwise, one closes housing opening 35. Protuberances 36, or other visual indicating means, coincide with the positioning of the end of door 66 which extends downward from cap 33. The larger the opening, the greater the amount of scented mist that will be released into the ambient atmosphere.

When sufficient scented mist has been released, one shuts the device off by switching on/off switch 34 to its "off" position, and any remaining vapor within mesh member 68 coalesces back to its liquid form which then drains downward through through drain opening 44, and also any liquid in nozzle member 62 drains back through tube 78 into bottle 20. The inside bottom portion 39 of side wall 38 of housing 12 can be sloped downward and inward to help drain the liquid into drain opening 44 which drain opening extends almost all the way around chamber housing 51 to promote drainage of any remaining scented liquid back into bottle 20. This drainage design prevents the scented quid from drying out on mesh member 68 and on the inner walls of housing 12 and after time from plugging up various apertures and reducing the efficiency of, the device as might otherwise occur without the drainage features of this invention.

Although the present invention has been described with reference to particular embodiments, it will be apparent to those skilled in the art that variations and modifications can be substituted therefor without departing from the principles and spirit of the invention.

We claim:

1. In combination, an air nebulizer for dispersing scented mist into ambient atmosphere having on/off switch means for an "on" mode and an "off" mode; pressurized air pump means; a hose member having a first end and a second end, said first end carrying said pressurized air from said pump means, and a bottle containing scented liquid, said bottle having a top, an inner wall, an opening defined at said top of said bottle, said bottle having normal atmospheric air pressure therein, further including:

a housing having a top portion, a bottom portion, an interior portion defined within said housing having interior walls, and a central vertical axis defined therethrough, said housing having means to engage said housing bottom portion into said opening of said top of said bottle;

air entrance means on said housing to engage said second end of said hose member to said housing to direct said pressurized air into said interior portion of said housing;

a chamber housing having a top and a bottom, said chamber housing having an open chamber defined centrally therein along a central vertical axis of the housing, said open chamber having a bottom portion communicating with said air entrance means to receive said pressurized air, said chamber housing disposed in said bottom portion of said housing, said chamber housing having a chamber aperture defined at said top of said chamber housing;

a nozzle member having an upper portion having a top and a bottom portion, said nozzle member having an interior defined therein, an exterior and a vertical axis defined therethrough, said nozzle member having an upper aperture defined at said top of said upper portion in line with said vertical axis, and a lower aperture defined at said bottom portion in line with said vertical axis in communication with said nozzle member's upper aperture, said nozzle member being disposed in said chamber, said upper portion being of a size smaller than dimensions of said chamber to allow said pressurized air to pass therearound and to enter said interior portion of said housing through said chamber aperture such air movement to lower the air pressure in said open chamber above said nozzle member upper aperture compared to the air pressure in said bottle with said bottom portion of said nozzle member blocking said bottom portion of said open chamber;

a tube disposed in said lower aperture of said nozzle member extending down to said scented liquid in said bottle, said lower air pressure in said chamber above said nozzle member upper aperture, causing said scented liquid in said bottle to be forced up said tube by the normal atmospheric pressure in said bottle to pass as a mist through said nozzle member upper aperture and through said chamber aperture into said interior portion of said housing;

a mesh member disposed within said interior portion of said housing filling a substantial portion of said interior portion of said housing above said chamber aperture;

an opening defined in said top portion of said housing;

means to adjust size of said opening defined in said top portion of said housing;

a drain opening defined in said bottom portion of said housing disposed substantially around said chamber housing;

whereby said device in its "on" mode forcing said scented liquid up through said nozzle member and out said chamber aperture as a mist into said housing and through said mesh member to be dispersed into finer particles of mist to be discharged through said adjustable opening at said top portion of said housing to add scented fine mist into said ambient atmosphere; and whereby said scented mist on said mesh member, when said device in its "off" mode, coalescing to form a liquid which drains through said drain opening back into said bottle for reuse.

2. The device of claim 1 wherein said open chamber and upper portion of said nozzle member are cylindrical, said open chamber having a diameter greater than a diameter of said upper portion of said nozzle member positioned therein, said bottom portion of said nozzle member blocking said bottom portion of said chamber housing.

3. The device of claim 2 wherein said interior of said nozzle member has downwardly sloped portions to promote downward drainage of said scented fluid remaining in said nozzle member when said device is in its "off" mode.

4. The device of claim 3 further including:

a bottle seat portion formed in said bottom portion of said housing to engage against said inner wall of said open top of said bottle; and wherein said interior walls in said bottom portion of said housing slope inwardly toward said drain opening to aid in draining scented fluid through said drain opening into said bottle when said device is in its "off" mode.

* * * * *